(12) United States Patent
Voskoboynikov et al.

(10) Patent No.: US 9,433,714 B2
(45) Date of Patent: Sep. 6, 2016

(54) SPEED CHANGE ALGORITHM FOR A CONTINUOUS FLOW BLOOD PUMP

(71) Applicant: HeartWare, Inc., Miami Lakes, FL (US)

(72) Inventors: Neil Voskoboynikov, Pembroke Pines, FL (US); Joel Graham, Sunny Isles, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/405,948

(22) PCT Filed: Jun. 6, 2013

(86) PCT No.: PCT/US2013/044540
§ 371 (c)(1),
(2) Date: Dec. 5, 2014

(87) PCT Pub. No.: WO2013/184932
PCT Pub. Date: Dec. 12, 2013

(65) Prior Publication Data
US 2015/0151032 A1 Jun. 4, 2015

Related U.S. Application Data

(60) Provisional application No. 61/656,342, filed on Jun. 6, 2012.

(51) Int. Cl.
*A61N 1/362* (2006.01)
*A61M 1/10* (2006.01)
*G06F 19/00* (2011.01)

(52) U.S. Cl.
CPC ........ *A61M 1/1086* (2013.01); *G06F 19/3406* (2013.01); *A61M 2205/3334* (2013.01); *A61M 2205/3365* (2013.01)

(58) Field of Classification Search
USPC ...................................... 600/16–17
See application file for complete search history.

(56) References Cited

U.S. PATENT DOCUMENTS 6,234,772 B1   5/2001   Wampler et al.
6,264,601 B1   7/2001   Jassawalla et al.

(Continued)

OTHER PUBLICATIONS

International Preliminary Report on Patentability with Annexed Amended Article 34 for Application No. PCT/US13/44540 dated Sep. 26, 2014.
International Search Report for Application No. PCT/US13/44540 dated Oct. 24, 2013.
Ranjit et al., "Aortic valve pathophysiology during left ventricular assist device support", The Journal of Heart and Lung Transplantation, vol. 29, No. 12, Dec. 2010.

(Continued)

*Primary Examiner* — Nicole F Lavert
(74) *Attorney, Agent, or Firm* — Lerner, David, Littenberg, Krumholz & Mentlik, LLP

(57) ABSTRACT

A ventricular assist device ("VAD") includes a continuous-flow pump (2) implantable in fluid communication with a ventricle (V) and an artery (A) of a patient to assist blood flow from the ventricle to the artery. The VAD also includes a control circuit (12) connected to the pump, the control circuit being configured to direct the pump to operate in a series of cycles. Each cycle may include (i) pumping blood at a first speed ($RPM_1$) and at a first flow rate during a first period ($t_1$); then (ii) decreasing the speed of the pump from the first speed to a second speed ($RPM_2$) during a ramp-down period ($t_{RD}$); then (iii) pumping blood at the second speed and at a second flow rate during a second period ($t_2$); and then (iv) increasing the speed of the pump from the second speed to the first speed during a ramp-up period ($t_{RU}$).

23 Claims, 3 Drawing Sheets

(56) References Cited

U.S. PATENT DOCUMENTS

| | | |
|---|---|---|
| 6,264,635 B1 | 7/2001 | Wampler et al. |
| 7,269,460 B2 | 9/2007 | Chinchoy |
| 7,699,586 B2 | 4/2010 | LaRose et al. |
| 7,963,905 B2 | 6/2011 | Salmonsen et al. |
| 8,562,507 B2 | 10/2013 | Poirier |
| 8,715,151 B2 | 5/2014 | Poirier |
| 2005/0071001 A1 | 3/2005 | Jarvik |
| 2005/0215843 A1* | 9/2005 | Medvedev ............ A61M 1/122 600/16 |
| 2009/0112312 A1 | 4/2009 | LaRose et al. |
| 2012/0078031 A1 | 3/2012 | Burke et al. |

OTHER PUBLICATIONS

Slaughter et al., "Clinical management of continous-flow left ventricular assist devices in advanced heart failure", The Journal Heart and Lung Transplantation, vol. 29, No. 45, Apr. 2010, pp. S1-S39.

Stainback et al., "Echocardiographic evaluation of the Jarvik 2000 Axial-Flow LVAD", Texas Heart Institute Journal, vol. 32, No. 3, 2005, pp. 263-270.

Tuzun et al., "The Effect of Intermittent Low Speed Mode Upon Aortic Valve Opening in Calves Supported with a Jarvik 2000 Axial Flow Device", ASAIO Journal 2005, pp. 139-143.

* cited by examiner

SPEED CHANGE ALGORITHM FOR A CONTINUOUS FLOW BLOOD PUMP

CROSS-REFERENCE TO RELATED APPLICATIONS

The present application is a national phase entry under 35 U.S.C. §371 of International Application No. PCT/US2013/044540 filed Jun. 6, 2013, published in English, which claims priority of the filing date of U.S. Provisional Application No. 61/656,342, filed Jun. 6, 2012, entitled SPEED CHANGE ALGORITHM FOR A CONTINUOUS FLOW BLOD PUMP, the disclosures of which are both hereby incorporated herein by reference.

BACKGROUND OF THE INVENTION

A ventricular assist device ("VAD") is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source.

VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal.

Aortic valve biomechanics in patients with VAD support may be altered. This can be due to continuous ventricular unloading and may affect aortic valve opening behavior during VAD support. These altered biomechanics may be associated with aortic insufficiency, stenosis, commissural fusion, and thrombus formation during VAD support. Long-term VAD support can increase the incidence of some of these complications. Adjusting the pump speed to allow periodic opening of the aortic valve may prevent the altered aortic valve biomechanics, including leaflet fusion, stasis in the aortic root, and formation of thrombus in the aorta. A previous approach to aiding aortic valve opening has been limited to operating VADs at minimal pump speeds. This previous approach minimizes perfusion and is a one-size-fits-all solution that does not account for specific patient requirements. Thus improvements are desirable.

BRIEF SUMMARY OF THE INVENTION

In one embodiment of the invention, a ventricular assist device ("VAD") includes a continuous-flow pump implantable in fluid communication with a ventricle and an artery of a patient to assist blood flow from the ventricle to the artery. The VAD also includes a control circuit connected to the pump, the control circuit being configured to direct the pump to operate in a series of cycles.

Each cycle may include (i) pumping blood at a first speed and at a first flow rate during a first period, then (ii) decreasing the speed of the pump from the first speed to a second speed during a ramp-down period; then (iii) pumping blood at the second speed and at a second flow rate during a second period; and then (iv) increasing the speed of the pump from the second speed to the first speed during a ramp-up period. The second speed may be a function of the first speed, and the second flow rate may be a net positive antegrade flow. Also, the first flow rate may be no more than 3 liters per minute greater than the second flow rate. Further, the first flow rate may be no more than 1 liter per minute greater than the second flow rate.

The second speed may be a linear function of the first speed. The second speed may between about 75% and about 90% of the first speed. The first period may be between about 5 seconds and about 30 seconds. In one example, the first period may be about 10 seconds and the ramp-down period, the second period, and the ramp-up period may total about 5 seconds.

The second speed may be about 80% or about 85% of the first speed. In another example, the first period may be about 30 seconds, and the ramp-down period, the second period, and the ramp-up period total about 5 seconds. In that example, the second speed may be about 85% of the first speed. In other examples, the ramp-down period, the second period, and the ramp-up period may total between about 4 seconds and about 10 seconds, or between about 5 seconds and about 6 seconds.

The control circuit may include a processor and a memory connected to the processor, the processor being operative to command the pump responsive to instructions stored in the memory. The memory having stored therein a first preset operating profile in which the first period is about 10 seconds, the ramp-down period, the second period, and the ramp-up period total about 5 seconds, and the second speed is about 80% of the first speed. The memory may also have stored therein a second preset operating profile in which the first period is about 10 seconds, the ramp-down period, the second period, and the ramp-up period total about 5 seconds, and the second speed is about 85% of the first speed. The memory may further have stored therein a third preset operating profile in which the first period is about 30 seconds, the ramp-down period, the second period, and the ramp-up period total about 5 seconds, and the second speed is about 85% of the first speed.

In another embodiment of the invention, a method of operating a VAD incorporating a continuous flow pump connected between an artery and a ventricle of a patient includes the steps of cyclically (i) pumping blood from the ventricle to the artery of the patient by operating a continuous flow pump at a first speed and at a first flow rate during a first period; then (ii) decreasing the speed of the pump from the first speed to a second speed during a ramp-down period; then (iii) pumping blood from the ventricle to the artery by operating the pump at the second speed and at a second flow rate less than the first flow rate during a second period; and then (iv) increasing the speed of the pump from the second speed to the first speed during a ramp-up period. The second speed may be selected so that pressure within the ventricle during systole occurring during the second period momentarily exceeds pressure within the artery thereby opening a valve between the ventricle and the artery, but so that the second flow rate is a net positive antegrade flow. Also, the first flow rate may be no more than 3 liters per minute greater than the second flow rate. Further, the first flow rate may be no more than 1 liter per minute greater than the second flow rate.

The second speed may be a function of the first speed, such as a linear function. The second speed may be between about 75% and about 90% of the first speed. The first period may be between about 5 seconds and about 30 seconds. In one example, the first period may be about 10 seconds and the ramp-down period, the second period, and the ramp-up period may total about 5 seconds. In that example, the second speed may be about 80% or about 85% the first speed. In another example, the first period may be about 30 seconds, and the ramp-down period, the second period, and the ramp-up period may total about 5 seconds. In that example, the second speed may be about 85% of the first speed. In other examples, the ramp-down period, the second period, and the ramp-up period may total between about 4 seconds and about 10 seconds, or between about 5 seconds and 6 seconds.

The method may further include the step of setting the first and second speeds and the first and second periods by choosing one of a plurality of preset operating profiles and actuating a control circuit associated with the pump to operate the pump according to the chosen profile. The plurality of preset operating profiles may include a first preset operating profile in which the first period is about 10 seconds, the ramp-down period, the second period, and the ramp-up period total about 5 seconds, and the second speed is about 80% of the first speed. The plurality of preset operating profiles may also include a second preset operating profile in which the first period is about 10 seconds, the ramp-down period, the second period, and the ramp-up period total about 5 seconds, and the second speed is about 85% of the first speed. The plurality of preset operating profiles may further include a third preset operating profile in which the first period is about 30 seconds, the ramp-down period, the second period, and the ramp-up period total about 5 seconds, and the second speed is about 85% of the first speed.

DETAILED DESCRIPTION

Figure 1:
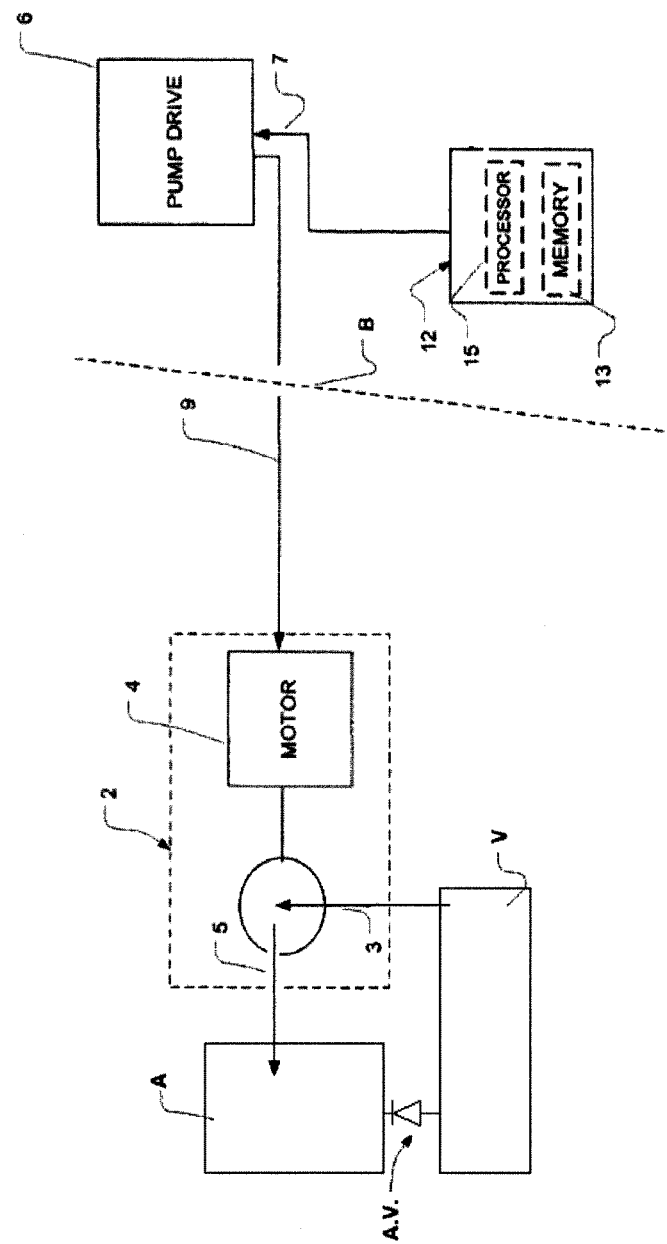
FIG. 1 is a diagrammatic view of a VAD with associated components.

A VAD according to one embodiment of the invention (FIG. 1) includes an implantable rotary pump 2, incorporating a motor 4. As used in this disclosure, the term "rotary pump" refers to a pump which incorporates a pumping element mounted for rotation in a housing. Most typically, the pump 2 is a rotary impeller pump having an impeller mounted within the housing, so that the spinning motion of the impeller transfers momentum to the fluid to be pumped. Although the pump 2 and motor 4 are depicted as separate components for clarity of illustration in FIG. 1, in practice these components can be closely integrated with one another. For example, the impeller of the pump 2 may serve as the rotor of the motor 4. Most typically, the motor 4 is a multi-phase alternating current, permanent magnet motor arranged to drive the impeller of the pump 2 at a rotational speed proportional to the frequency of the current supplied to the motor 4. Pump 2 has a fluid inlet 3 and a fluid outlet 5. These components are arranged so that the pump 2 can be implanted within the body of a mammalian subject such as a human patient, with the inlet 3 in fluid communication with a ventricle V of the heart, most typically the left ventricle, and with the outlet 5 in fluid communication with an artery A, most typically the aorta. The ventricle V and artery A may be separated by a valve, such as the aortic valve A.V., as illustrated in FIG. 1. For example, the pump 2 may be arranged for implantation outside of the heart, and the inlet and outlet may include conduits that can be surgically connected to the ventricle and the aorta. In other arrangements, the pump 2 is arranged so it can be implanted within the aorta and ventricle. Implantable pumps are described in detail in U.S. Pat. Nos. 6,264,635, 6,234,772 and 7,699,586; and US Patent Publication No. 2009/0112312. These patents and published patent applications, which are commonly assigned, are hereby incorporated by reference herein.

The VAD also includes a pump drive circuit 6. The pump drive circuit 6 may include an electrical storage battery and an inverter for generating an alternating current. The output of the inverter is connected by an output connection, such as a cable 9 to the motor 4 of pump 2, so that the alternating current supplied by the power source can drive the motor 4 and thus operate the pump 2. The inverter typically includes semiconductor switching elements which are responsive to control signals applied at a control input 7, so that the frequency of the alternating current supplied to motor 4 can be controlled. In the particular arrangement depicted, pump drive circuit 6 is mountable outside of the patient's body B and is connected to the motor 4 by conductors which penetrate the skin of the patient. In other arrangements, the pump drive circuit 6 may be implanted within the body B and may be connected to an external power source by an inductive coupling or skin-penetrating conductors.

The VAD also includes a control circuit 12. As illustrated in FIG. 1, control circuit 12 may be external to the body B, and may, for example, be part of an external handheld controller. However, the control circuit 12 may be implantable in the body B and may, for example, be part of the pump 2. The control circuit 12 is connected to the control input 7 of pump drive circuit 6.

Control circuit 12 may include conventional data processing elements such as one or more processors 15 and one or more memory elements 13 arranged to perform the algorithms discussed below. In other embodiments, the control circuit may include other structures capable of performing the algorithm discussed below, such as analog timers and switches, or programmable devices such as programmable gate array logic.

During operation of a VAD, when the motor 4 is operating at a high speed of rotation and the pump 2 is outputting blood at a high flow rate, the pressure in the ventricle V during systole may be low compared to the pressure within the artery A. This may result in a valve between the ventricle V and the artery A, such as the aortic valve A.V., remaining closed during operation of the VAD. As noted in the background, if the aortic valve A.V. remains shut for long periods of time, leaflet fusion, stasis in the aortic root, and formation of thrombus in the aorta may occur.

The speed control algorithm in the control circuit 12 directs the pump 2 via the pump drive 6 to operate in a series of cycles. Portions of two exemplary cycles are illustrated in FIG. 2.

Figure 2:
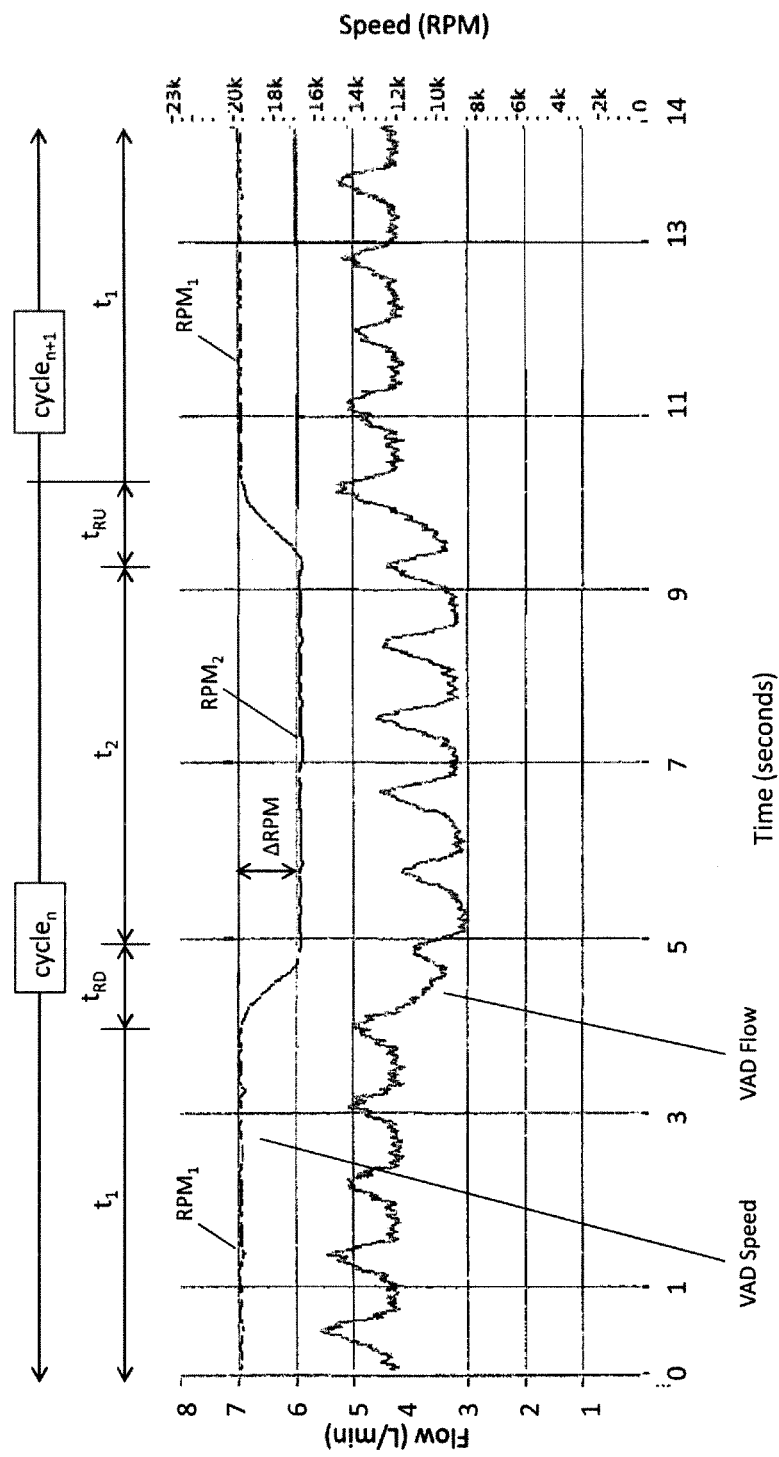
FIG. 2 is a graph illustrating the cyclical flow and speed levels in a VAD using a speed control algorithm.

Now referring to FIG. 2, a graph of VAD speed (in RPMs) and blood flow (in L/min) is illustrated as a function of time (in seconds). VAD speed and blood flow are illustrated for an end portion of a first cycle n and for a beginning portion of a second cycle n+1. Each cycle includes a first period $t_1$ during which the pump 2 operates at a first speed $RPM_1$. The first speed $RPM_1$ may be, for example, a speed determined by a physician to provide adequate blood flow characteristics for a specific patient using a particular type of pump. As such, different patients with different particular physiologies may have pumps with different values for the first speed $RPM_1$.

After the first period $t_1$ comes to an end, the control circuit 12 directs the pump 2 to reduce its speed by a magnitude $\Delta RPM$ to a second speed $RPM_2$. However, because the pump has a finite response time, this reduction in speed is not instantaneous, but rather occurs over a ramp-down period $t_{RD}$. Once the pump 2 reaches the second speed $RPM_2$, the pump 2 continues at that speed for a second period $t_2$. In practice, the control circuit 12 need not direct the pump 2 to first ramp-down, and then maintain the second speed $RPM_2$. As illustrated in FIG. 2, as the pump speed decreases, a corresponding decrease in the flow rate of the pump 2 occurs.

After the combined duration of the ramp-down period $t_{RD}$ and the second period $t_2$ comes to an end, the control circuit 12 directs the pump 2 to increase its speed back to the first speed $RPM_1$.

Again, as discussed above, the increase in speed is generally not instantaneous and thus a ramp-up period $t_{RU}$ occurs during which the pump speed increases to the first speed $RPM_1$. The next cycle of operation (cycle n+1) begins when the pump reaches the first speed $RPM_1$.

Figure 3:
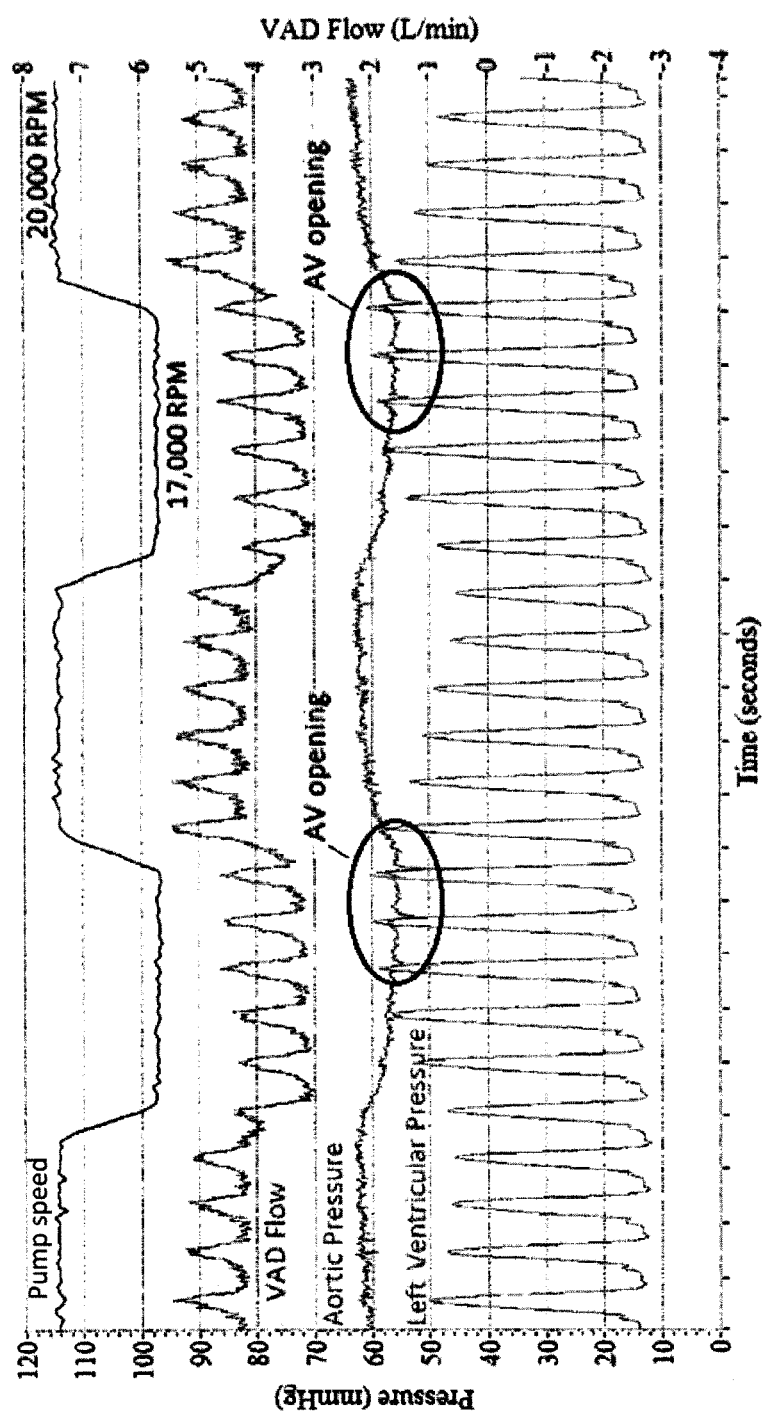
FIG. 3 is a graph illustrating the cyclical flow and speed levels in a VAD, including aortic and ventricular pressure levels, in a VAD using a speed control algorithm.

The effects of an exemplary cycling of the speed of the pump 2 are best illustrated in FIG. 3.

This particular illustration includes a pump speed cycling from a first speed $RPM_1$ of 20,000 RPM to a second speed $RPM_2$ of 17,000 RPM. When the pump speed is at a first relatively high speed $RPM_1$ of 20,000 RPM, the flow rate is a first, relatively high rate, and the aortic pressure is greater than the maximum left ventricular pressure during systole. As the speed of the pump drops and remains at the reduced second speed $RPM_2$ of 17,000 RPM, the flow rate decreases, while the aortic pressure drops and the maximum left ventricular pressure increases.

As indicated in FIG. 3, the maximum left ventricular pressure during systole eventually increases above the aortic pressure. When the maximum left ventricular pressure is above the aortic pressure, during which time the aortic valve A.V. opens during each cardiac cycle. This condition prevails until the increase in pump speed near the end of the pump cycle discussed above raises the aortic pressure and reduces the maximum left ventricular pressure.

The flow rate through the pump is only minimally reduced such that valve opening periodically occurs but perfusion remains relatively high. For example, the net antegrade flow of blood through the pump and the heart preferably remains positive (i.e. no retrograde flow) when the pump speed is reduced to the second speed $RPM_2$. More preferably, the flow rate during the first period $t_1$ with a relatively high pump speed $RPM_1$ and the flow rate during the second period $t_2$ with a relatively low pump speed $RPM_2$ differ by no more than 3 liters per minute. Most preferably, the flow rates during periods of high pump speed $RPM_1$ and reduced pump speed $RPM_2$ differ by 1 liter per minute or less. This net positive flow of blood and the preferably small difference in flow rates allow adequate perfusion to occur during the cycles of pumping while still allowing the aortic valve A.V. to open periodically.

According to another aspect of the invention, the change in magnitude $\Delta RPM$ between the first flow rate $RPM_1$ and the second flow rate $RPM_2$ may be based on the magnitude of the first flow rate $RPM_1$. Rather than using a particular number of RPMs to reduce the first flow rate $RPM_1$, the reduction is based on the magnitude of $RPM_1$, so that the second pump speed $RPM_2$ is a function of the first pump speed. This may, for example, take into account different physiologies of different patients that have different set speeds of pump operation. For example, the relationship between the first speed $RPM_1$ and the second speed $RPM_2$ may be a linear function of $RPM_1$. In an example of a linear relationship, the second speed $RPM_2$ is set as a percentage of the first speed $RPM_1$. Preferably, the second speed $RPM_2$ is between about 75% and about 90% of the first speed $RPM_1$. More preferably, the second speed $RPM_2$ is about 80% or about 85% of the first speed $RPM_1$ According to a further aspect of the invention, the duration of the first period $t_1$ in which the pump operates at the first speed $RPM_1$ and the duration of the time during which the pump operates at a decreased speed, including the ramp-down period $t_{RD}$, the second period $t_2$, and the ramp-up period $t_{RU}$, may also be precisely controlled to optimize perfusion and valve opening. Preferably, the first period $t_1$ is between about 5 seconds and about 30 seconds.

More preferably, the first period is about 10 seconds. Further, the total duration of the ramp-down period $t_{RD}$, the second period $t_2$, and the ramp-up period $t_{RU}$, is preferably between about 4 seconds and about 10 seconds, most preferably between about 5 seconds and about 6 seconds. Although the invention is not strictly limited to the exemplary values listed above, they have been shown to be particularly effective at maintaining sufficient perfusion while maintaining periodic valve opening.

In still a further embodiment of the invention, the memory 13 includes instructions in the form of preset operating profiles. A user can choose a particular preset operating profile, for example, depending on the experience of the physician or particular physiology of the patient, to cause the processor 15 to instruct the pump 2 to operate using predefined parameters. For example, the memory 13 may have stored therein three preset operating profiles, including a "high," "medium," and "low" profile, as illustrated in Table 1.

TABLE 1

| Profile | % Speed Drop | Speed Drop Duration [tRD + t2 + tRU] (seconds) | Cycle Interval [t1] (seconds) |
| --- | --- | --- | --- |
| High | 20 | 5 | 10 |
| Medium | 15 | 5 | 10 |
| Low | 15 | 5 | 30 |

As illustrated in Table 1, the three preset operating profiles may range from "high" to "low," with the "high" profile inducing the most frequent and intense speed drops, with the "low" profile inducing the least frequent and least intense speed drops.

According to the above example, the "high" profile includes a speed drop of about 20%, wherein the second speed $RPM_2$ is about 80% the value of the first speed $RPM_1$. The first time period $t_1$ in which the pump speed is the first speed $RPM_1$ is about 10 seconds. The remaining time in the cycle in which the speed is less than the first speed $RPM_1$ is about 5 seconds, including the ramp-down period $t_{RD}$, the second period $t_2$, and the ramp-up period $t_{RU}$. This relatively large speed drop will cause the greatest increase in left ventricular pressure compared to aortic pressure during systole during the lower speed operation, causing the most forceful valve opening. Also, the duration of the first period $t_1$ is relatively short, resulting in more frequent valve opening.

Still referring to Table 1, the "medium" profile includes a speed drop of about 15%, wherein the second speed $RPM_2$ is about 85% the value of the first speed $RPM_1$. The first time period $t_1$ in which the pump speed is the first speed $RPM_1$ is about 10 seconds. The remaining time in the cycle in which the speed is less than the first speed $RPM_1$ is about 5 seconds, including the ramp-down period $t_{RD}$, the second period $t_2$, and the ramp-up period $t_{RU}$. This speed drop is less than the "high" profile, causing a lower increase in left ventricular pressure compared to aortic pressure during systole during the lower speed operation, causing somewhat less forceful valve opening. Also, the duration of the first period $t_1$ is the same as the "high" profile, resulting in valve opening at a similar frequency.

Still referring to Table 1, the "low" profile includes a speed drop of about 15%, wherein the second speed $RPM_2$ is about 85% the value of the first speed $RPM_1$. The first time period $t_1$ in which the pump speed is the first speed $RPM_1$ is about 30 seconds. The remaining time in the cycle in which the speed is less than the first speed $RPM_1$ is about 5 seconds, including the ramp-down period $t_{RD}$, the second period $t_2$, and the ramp-up period $t_{RU}$. This speed drop is the same as the "medium" profile, causing a similar increase in left ventricular pressure compared to aortic pressure during systole during the lower speed operation, causing similarly forceful valve opening. However, the duration of the first period $t_1$ is longer than both the "high" and "medium" profiles, resulting in the least frequent valve opening.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A ventricular assist device comprising:
a continuous-flow pump implantable in fluid communication with a ventricle and an artery of a patient to assist blood flow from the ventricle to the artery;
a control circuit connected to the pump, the control circuit being configured to direct the pump to operate in a series of cycles, each cycle including:
(i) pumping blood at a first speed and at a first flow rate during a first period; then
(ii) decreasing the speed of the pump from the first speed to a second speed during a ramp-down period; then
(iii) pumping blood at the second speed and at a second flow rate during a second period; and then
(iv) increasing the speed of the pump from the second speed to the first speed during a ramp-up period,
wherein the second speed is a function of the first speed, the second speed is selected so that pressure within the ventricle during systole occurring during the second period momentarily exceeds pressure within the artery thereby opening a native aortic valve between the ventricle and the artery, and the second flow rate is a net positive antegrade flow;
wherein the first speed of each cycle is substantially the same as the first speed of every other cycle, and the second speed of each cycle is substantially the same as the second speed of every other cycle.

2. The ventricular assist device of claim 1, wherein the second speed is a linear function of the first speed.

3. The ventricular assist device of claim 2, wherein the second speed is between about 75% and about 90% of the first speed.

4. The ventricular assist device of claim 1, wherein the first period is between about 5 seconds and about 30 seconds.

5. The ventricular assist device of claim 4, wherein the ramp-down period, the second period, and the ramp-up period total about 5 seconds.

6. The ventricular assist device of claim 5, wherein the second speed is about 80% of the first speed.

7. The ventricular assist device of claim 5, wherein the second speed is about 85% of the first speed.

8. The ventricular assist device of claim 1, wherein the ramp-down period, the second period, and the ramp-up period total between about 4 seconds and about 10 seconds.

9. The ventricular assist device of claim 1, wherein the control circuit includes a processor and a memory connected to the processor, the processor being operative to command the pump responsive to instructions stored in the memory, the memory having stored therein:
(i) a first preset operating profile in which the first period is about 10 seconds, the ramp-down period, the second period, and the ramp-up period total about 5 seconds, and the second speed is about 80% of the first speed,
(ii) a second preset operating profile in which the first period is about 10 seconds, the ramp-down period, the second period, and the ramp-up period total about 5 seconds, and the second speed is about 85% of the first speed, and
(ill) a third preset operating profile in which the first period is about 30 seconds, the ramp-down period, the second period, and the ramp-up period total about 5 seconds, and the second speed is about 85% of the first speed.

10. The ventricular assist device of claim 1, wherein the first flow rate is no more than 3 liters per minute greater than the second flow rate.

11. A method of operating a ventricular assist device incorporating a continuous flow pump connected between an artery and a ventricle of a patient comprising the steps of cyclically:
(i) pumping blood from the ventricle to the artery of the patient by operating a continuous flow pump at a first speed and at a first flow rate during a first period; then
(ii) decreasing the speed of the pump from the first speed to a second speed during a ramp-down period; then
(iii) pumping blood from the ventricle to the artery by operating the pump at the second speed and at a second flow rate less than the first flow rate during a second period; and then
(iv) increasing the speed of the pump from the second speed to the first speed during a ramp-up period,
wherein the second speed is selected so that pressure within the ventricle during systole occurring during the second period momentarily exceeds pressure within the artery thereby opening a native aortic valve between the ventricle and the artery, but so that the second flow rate is a net positive antegrade flow;
wherein the first speed of each cycle is substantially the same as the first speed of every other cycle, and the second speed of each cycle is substantially the same as the second speed of every other cycle.

12. The method of claim 11, wherein the second speed is a linear function of the first speed.

13. The method of claim 12, wherein the second speed is between about 75% and about 90% of the first speed.

14. The method of claim 11, wherein the first period is between about 5 seconds and about 30 seconds.

15. The method of claim 14, wherein the ramp-down period, the second period, and the ramp-up period total about 5 seconds.

16. The method of claim 15, wherein the second speed is about 80% of the first speed.

17. The method of claim 15, wherein the second speed is about 85% of the first speed.

18. The method of claim 11, wherein the ramp-down period, the second period, and the ramp-up period total between about 4 seconds and about 10 seconds.

19. The method of claim 11, further comprising the step of setting the first and second speeds and the first and second periods by choosing one of a plurality of preset operating profiles and actuating a control circuit associated with the pump to operate the pump according to the chosen profile.

20. The method of claim 19, wherein the plurality of preset operating profiles includes:

(i) a first preset operating profile in which the first period is about 10 seconds, the ramp-down period, the second period, and the ramp-up period total about 5 seconds, and the second speed is about 80% of the first speed, (ii) a second preset operating profile in which the first period is about 10 seconds, the ramp-down period, the second period, and the ramp-up period total about 5 seconds, and the second speed is about 85% of the first speed, and (iii) a third preset operating profile in which the first period is about 30 seconds, the ramp-down period, the second period, and the ramp-up period total about 5 seconds, and the second speed is about 85% of the first speed.

21. The method of claim 11, wherein the first flow rate is no more than 3 liters per minute greater than the second flow rate.

22. The ventricular assist device of claim 1, wherein the first and second speeds predetermined.

23. The method of claim 11, wherein the first and second speeds are predetermined.

\* \* \* \* \*